(12) United States Patent
Stefanchik et al.

(10) Patent No.: US 9,066,655 B2
(45) Date of Patent: Jun. 30, 2015

(54) SELECTIVE STIFFENING DEVICES AND METHODS

(75) Inventors: David Stefanchik, Morrow, OH (US); Ragae M. Ghabrial, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1996 days.

(21) Appl. No.: 11/952,475

(22) Filed: Dec. 7, 2007

(65) Prior Publication Data

US 2009/0149710 A1 Jun. 11, 2009

(51) Int. Cl.
| | |
|---|---|
| A61B 1/00 | (2006.01) |
| A61B 1/04 | (2006.01) |
| A61M 31/00 | (2006.01) |
| A61M 37/00 | (2006.01) |
| A61B 1/005 | (2006.01) |

(52) U.S. Cl.
CPC ............. *A61B 1/005* (2013.01); *A61B 1/00078* (2013.01); *A61B 1/00147* (2013.01)

(58) Field of Classification Search
CPC ........... A61B 1/00078; A61B 1/00087; A61B 1/00131; A61B 1/00133; A61B 1/00135; A61B 1/00154; A61B 1/0051; A61B 1/0052; A61B 1/0053; A61B 1/0058; A61B 1/008; A61B 1/01; A61B 1/012; A61B 1/0125; A61B 1/018; A61B 1/31; A61M 25/0122; A61M 25/0116; A61M 25/0158; A61M 25/0147
USPC ......... 600/114, 130, 143, 144, 104, 106, 115, 600/121–125, 151, 152; 604/95.01–95.05
See application file for complete search history.

(56) References Cited

U.S. PATENT DOCUMENTS

| | | | | |
|---|---|---|---|---|
| 3,258,883 | A | * | 7/1966 | Campanaro et al. ........... 52/2.16 |
| 4,815,450 | A | * | 3/1989 | Patel ............................. 600/115 |
| 5,025,778 | A | | 6/1991 | Silverstein et al. |
| 5,337,733 | A | * | 8/1994 | Bauerfeind et al. .......... 600/139 |
| 5,620,408 | A | * | 4/1997 | Vennes et al. ................. 600/114 |
| 5,759,151 | A | * | 6/1998 | Sturges ......................... 600/146 |
| 5,813,061 | A | * | 9/1998 | Tornqvist ........................... 4/431 |
| 6,179,776 | B1 | | 1/2001 | Adams et al. |
| 6,463,699 | B1 | * | 10/2002 | Bailey et al. ................... 52/2.11 |
| 6,672,338 | B1 | | 1/2004 | Esashi et al. |

(Continued)

OTHER PUBLICATIONS

U.S. Appl. No. 11/707,831, Stokes et al.

(Continued)

*Primary Examiner* — Ryan Henderson

(57) ABSTRACT

Methods and devices are provided for selectively stiffening a surgical device. In one exemplary embodiment a surgical device is provided that includes a flexible elongate insertion element and a stiffening element that extends along at least a portion of the insertion element. The insertion element can be, for example, an endoscope or a sheath configured to be disposed over an endoscope. The stiffening element can be configured to selectively stiffen when an outside force, such as a vacuum force, is applied thereto. In one embodiment the stiffening element includes a plurality of elongate members disposed in a flexible sheath. When the vacuum force is applied, the sheath can be configured to engage the elongate members to maintain the elongate members in a fixed, stiffened position, thereby stiffening at least a portion of the flexible elongate insertion element coupled thereto. Various methods for stiffening an insertion instrument, such as an endoscope, are also provided herein.

16 Claims, 19 Drawing Sheets

(56) References Cited

U.S. PATENT DOCUMENTS

| | | |
|---|---|---|
| 6,783,491 B2 | 8/2004 | Saadat et al. |
| 6,790,173 B2 | 9/2004 | Saadat et al. |
| 6,837,846 B2 | 1/2005 | Jaffe et al. |
| 6,837,847 B2 | 1/2005 | Ewers et al. |
| 6,878,106 B1* | 4/2005 | Herrmann ............. 600/104 |
| 6,984,203 B2* | 1/2006 | Tartaglia et al. ............ 600/114 |
| 7,914,445 B2* | 3/2011 | Smith et al. ............ 600/114 |
| 2004/0054322 A1* | 3/2004 | Vargas ............ 604/95.04 |
| 2004/0138525 A1 | 7/2004 | Saadat et al. |
| 2004/0138529 A1 | 7/2004 | Wiltshire et al. |
| 2004/0186350 A1 | 9/2004 | Brenneman et al. |
| 2004/0199052 A1 | 10/2004 | Banik et al. |
| 2004/0249367 A1 | 12/2004 | Saadat et al. |
| 2005/0065397 A1 | 3/2005 | Saadat et al. |
| 2005/0154258 A1* | 7/2005 | Tartaglia et al. ............ 600/114 |
| 2005/0250990 A1 | 11/2005 | Le et al. |
| 2005/0272977 A1 | 12/2005 | Saadat et al. |
| 2006/0015038 A1* | 1/2006 | Weymarn-Scharli ........ 600/585 |
| 2006/0069346 A1* | 3/2006 | Smith et al. ............ 604/95.05 |
| 2006/0178562 A1 | 8/2006 | Saadat et al. |
| 2008/0200762 A1* | 8/2008 | Stokes et al. ............ 600/139 |
| 2009/0030282 A1* | 1/2009 | Garcia et al. ............ 600/146 |
| 2009/0149710 A1* | 6/2009 | Stefanchik et al. ............ 600/146 |
| 2010/0069716 A1* | 3/2010 | Chin et al. ............ 600/114 |
| 2010/0152537 A1* | 6/2010 | Kobayashi ............ 600/115 |

OTHER PUBLICATIONS

Miller, Gavin; reference material found at website: http://www.snakerobots.com/, 1994 through 2007, 46 pages.

Piquepaille, Roland, "A Snake-Shaped Serpentine Robot for Rugged Terrain", from website http://www.primidi.com/2005/03/23.html, 2007, 5 pages.

Harris Tactical Group, "Snake-like Robots for Search & Rescue Missions", from website http://www.tactical-life.com/online/news/snake-like-robots-for-search-rescue-missions/??right=news, 2008, 3 pages.

"i-Snake Robot to Offer Slithering Assistance During Surgery", article from website http://gizmodo.com/338982/i+snake-robot-to-offer-slithering-assistance-during-surgery, 2008, 4 pages.

University of Michigan News Service, Press Release "Snake-like Robot Conquers Obstacles", from website http://www.ns.umich.edu/htdocs/releases/print.php?Releases/2005/Mar05/r032205b; Mar. 22, 2005, 5 pages.

University of Michigan, "Innovative Mobile Robots" and related reference material from OmniTread website: http://www.engin.umich.edu/research/mrl/OmniTread.html, 6 pages.

Granosik, et al., "The OmniTread Serpentine Robot for Industrial Inspection and Surveillance", *Intl. Journal on Industrial Robots, Special Issue on Mobile Robots*, vol. IR32-2, Mar. 18, 2005; pp. 139-148.

* cited by examiner

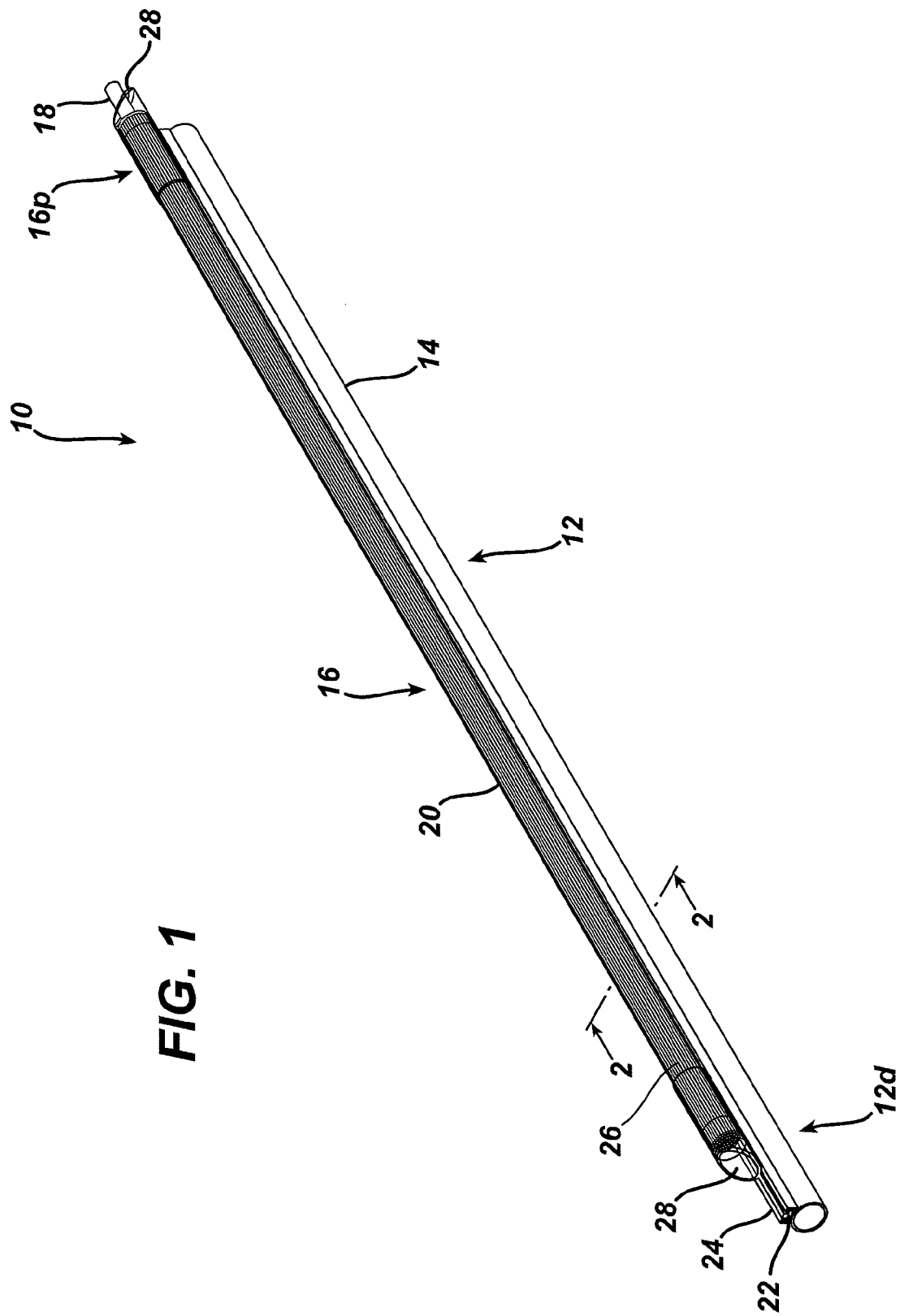

SELECTIVE STIFFENING DEVICES AND METHODS

FIELD

The present disclosure relates to apparatuses and methods for control and use of a surgical device during endoscopic or laparoscopic procedures.

BACKGROUND

Minimally invasive surgical techniques such as endoscopies and laparoscopies are often preferred over traditional open surgeries because the recovery time, pain, and surgery-related complications are typically less with minimally invasive surgical techniques. Rather than cut open large portions of the body in order to access inner cavities, such as the peritoneal cavity, surgeons either rely on natural orifices of the body or create one or more small orifices in which surgical instruments can be inserted to allow surgeons to visualize and operate at the surgical site. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the instruments used in such procedures. These instruments need to be suitable for precise placement of a working end at a desired surgical site to allow the surgeon to see the site and perform the necessary actions at such site. Often times the instruments either themselves contain a device that allows the surgeon to see the site, or else the instruments are used in conjunction with an instrument that can provide visual assistance. At least one of these types of devices, an endoscope, is typically configured with both a lens to visualize the surgical site and a channel through which instruments can be delivered to the surgical site for subsequent use. The instruments themselves can be used to engage and or treat tissue and other portions within the body in a number of different ways to achieve a diagnostic or therapeutic effect.

Minimally invasive procedures normally require that the shaft of any device inserted into the body be flexible to navigate the various shapes within the anatomy while still allowing stability and precision at the working end. During an endoscopy, for example, it is often necessary to navigate a device in a variety of different directions before the device reaches its desired destination, which means it is desirable that any such device be flexible. However, once the desired destination is reached, it is just as desirable that the device is strong and stable so that the surgeon can operate with precision. It is often difficult for the device to be strong and stable in a body cavity because body cavities generally include a large amount of three-dimensional space, which in turn means that there is not much in the way of support within the cavity that the device can rely upon for strength and stability. Still further, even when the original desired destination is reached, it is often the case that the surgeon will want to move the device during the course of the procedure, thus it is desirable that the device can easily be toggled between a flexible and a stationary state. It is also desirable that portions of the device can remain in a stationary state while other portions, most often the end closest to the surgical site, can be selectively flexible and stationary.

Accordingly, there remains a need for improved devices and methods for controlling surgical devices used during surgical procedures.

SUMMARY

Methods and devices are generally provided for selectively stiffening an insertion device during a surgical procedure. In one embodiment a stiffening element is provided for selectively stiffening a flexible elongate insertion element. The stiffening element can extend along at least a portion of the insertion element, and it can be configured to selectively stiffen when a vacuum force is applied to it. In one exemplary embodiment, the stiffening element includes a flexible sheath and a plurality of elongate members disposed within the flexible sheath. Alternatively, the stiffening element can include a flexible sheath and a plurality of discrete elements disposed within the flexible sheath. The flexible sheath can be elastic, and in use it can be configured to engage and prevent movement of the elongate members and/or discrete elements when a vacuum force is applied to the stiffening element. In another embodiment the elongate members and/or the discrete elements are configured to generate friction therebetween. The elongate members can, for example, be a plurality of wires and/or planar strips. In certain exemplary embodiments, the stiffening element is slidably coupled to the insertion element, for example using mating elements extending along external surfaces of the stiffening element and the insertion element. As for the insertion element, in one exemplary embodiment the insertion element can be an endoscope. In another embodiment the insertion element can be a sleeve configured to be disposed around an instrument, such as an endoscope. In still another embodiment, the surgical device can include a second stiffening element that extends along at least a portion of the flexible insertion element and that selectively stiffens when a vacuum force is applied thereto.

In another embodiment, a surgical device is provided for selective stiffening and it includes a stiffening element coupled to an elongate shaft. In one exemplary embodiment the stiffening element can move between a first position, in which the stiffening element is flexible, and a second position, in which a vacuum force applied to the stiffening element can cause the stiffening element to be rigidly maintained. Because of the coupling between the stiffening element and the elongate shaft, at least a portion of the elongate shaft can be maintained in a desired fixed position when the stiffening element is in the second position.

A method for selectively stiffening a surgical device is also provided. In one exemplary embodiment, a flexible elongate shaft can be inserted into a body cavity and a vacuum force can be applied to a stiffening element that is coupled to at least a portion of the flexible elongate shaft. The vacuum force can cause the stiffening element to become substantially rigid, which in turn can maintain at least a portion of the flexible elongate shaft in a fixed position. In one embodiment the stiffening element can be moved relative to the elongate flexible shaft. Alternatively, the elongate flexible shaft can be moved relative to the stiffening element. The method can also include flexing the elongate shaft as it is inserted into the body cavity and then maintaining the elongate shaft in a flexed position by applying a vacuum force to the stiffening element. A second stiffening element can also be introduced by coupling it to at least a portion of the flexible elongate shaft. A vacuum force can then be applied to the second stiffening element to cause the second stiffening element to become substantially rigid, which in turn can maintain at least a portion of the flexible elongate shaft in the fixed position. In one exemplary embodiment that includes both the first and second stiffening elements, the first and second stiffening elements can be moved sequentially relative to the flexible elongate shaft and sequentially stiffened by a vacuum force to move the flexible elongate shaft relative to the body cavity.

BRIEF DESCRIPTION OF DRAWINGS

The invention will be more fully understood from the following detailed description taken in conjunction with the accompanying drawings, in which:

FIG. 1 is a semi-transparent side perspective view of one exemplary embodiment of an insertion device and a stiffening element coupled thereto for selectively stiffening at least a portion of the insertion device;

DETAILED DESCRIPTION

Figure 2A:
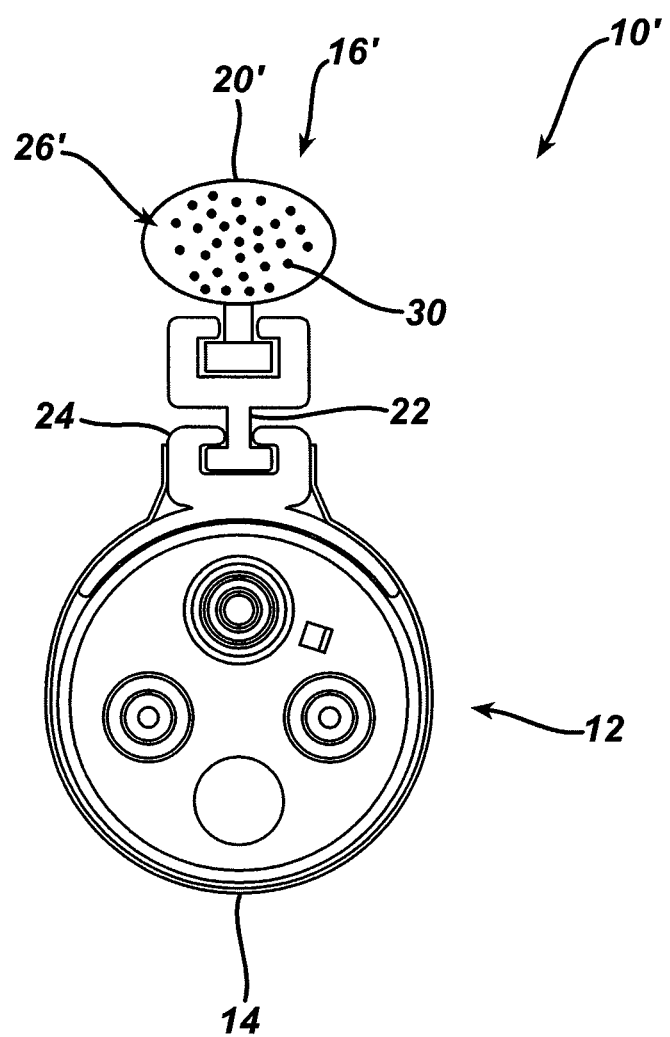
FIG. 2A is a front cross-sectional view of the apparatus of FIG. 1.
Figure 2B:
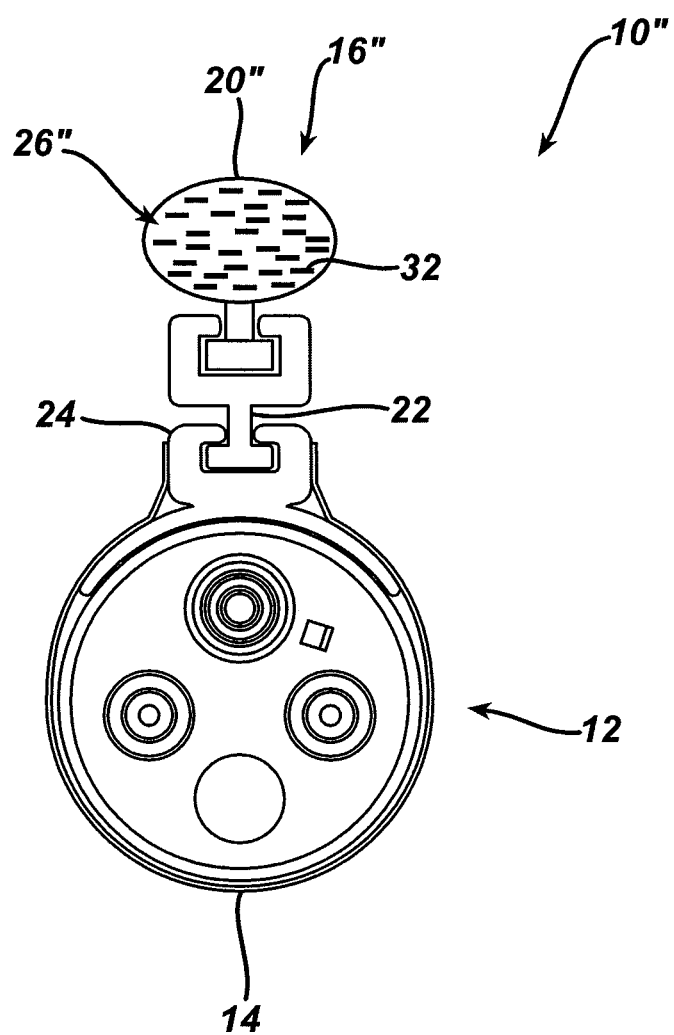
FIG. 2B is a front cross-sectional view of another exemplary embodiment of an insertion device and a stiffening element coupled thereto for selectively stiffening at least a portion of the insertion device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A stiffening element is generally provided for stiffening various insertion devices, such as endoscopes and laparoscopes. The stiffening element can be configured to extend along at least a portion of the insertion element such that when the stiffening element is selectively stiffened by an outside force, a portion of the insertion element can be maintained in a desired configuration. This allows the stiffening element to act as a support structure for the insertion element, thus allowing a distal end of the insertion element to be more precisely controlled to perform various procedures. The association between the stiffening element and the insertion element can be accomplished in any number of ways, but in one exemplary embodiment the stiffening element is slidably coupled to the insertion element. Together, the stiffening element and the insertion element can operate as a surgical device, allowing the stiffening element to selectively stiffen and unstiffen the insertion element as the insertion element is moved and used in the body during a surgical procedure. The stiffening element is especially useful with an insertion element in a three dimensional space, such as a peritoneal cavity, because such spaces do not generally provide structure that is useful for supporting an insertion element at the surgical site.

As indicated above, using the stiffening element to selectively stiffen local portions of an insertion element allows the insertion element to effectively be located at a fixed surgical site while still having the mobility to move within the surgical site and become fixed as desired. Further, the stiffening element can also assist in steering and/or extending the insertion element to a desired location. In particular, the ability to selectively stiffen the stiffening element can be useful when navigating the anatomy of the human body to reach a desired surgical site. Once the desired surgical site is reached, selective stiffening of the stiffening element can assist in extending the insertion element beyond the original surgical site. For example, if tissue is to be cut at a surgical site, the stiffening element can be selectively stiffened to assist in moving the insertion element, which in this instance would include a tool for cutting, to the general surgical site. Once the general surgical site is reached, the stiffening element can be stiffened to make the insertion element stationary at the general surgical site, and then the working end of the insertion element, which includes the tool for cutting, can be unstiffened and stiffened to allow the insertion element to move and be stationary as desired to perform the cutting actions.

FIGS. 1-4 illustrate various exemplary embodiments of a stiffening element 16, 16', 16" that is configured to extend along at least a portion of a flexible elongate insertion element 12 and that is configured to be selectively stiffened by an outside force. The combination of the stiffening element 16, 16', 16" and the insertion element 12 can be referred to as a device 10, 10', and 10". In general, the stiffening element 16, 16', 16" is configurable between a first position, in which the stiffening element 16, 16', 16" is flexible, and a second position, in which the stiffening element 16, 16', 16" is rigidly maintained in a desired position, i.e. it is stiffened. In an exemplary embodiment, the outside force used to selectively stiffen the stiffening element 16, 16', 16" is a vacuum force. Maintaining the stiffening element 16, 16', 16" in the desired position can likewise maintain the insertion element 12 in a desired configuration at least because they can be coupled together.

The stiffening element 16, 16', 16" can have a variety of configurations. In one exemplary embodiment the stiffening element 16, 16', 16" can include a flexible sheath 20, 20', 20". In the illustrated embodiments the flexible sheath 20, 20', 20" is tubular in shape, hollow, and it has a length. The length can be any desired length, which will likely depend, at least in part, on the desired use. For example, the flexible sheath 20, 20', 20" can be long enough to extend from a surgical site to a location outside of a body. Alternatively, the flexible sheath 20, 20', 20" can extend from a surgical site to an operator, thus allowing the operator to control and guide the flexible sheath 20, 20', 20". Meanwhile, the flexibility of the sheath 20, 20', 20" can result from a number of different properties, but in one embodiment the flexible sheath 20, 20', 20" can be elastic. Further, the flexibility of the sheath 20, 20', 20" can also be formed from a number of different materials, but in one embodiment the sheath 20, 20', 20" is formed from polymeric film. By way of non-limiting example, suitable polymers include Poly Ethylene and Poly Urethanes.

Figure 3:
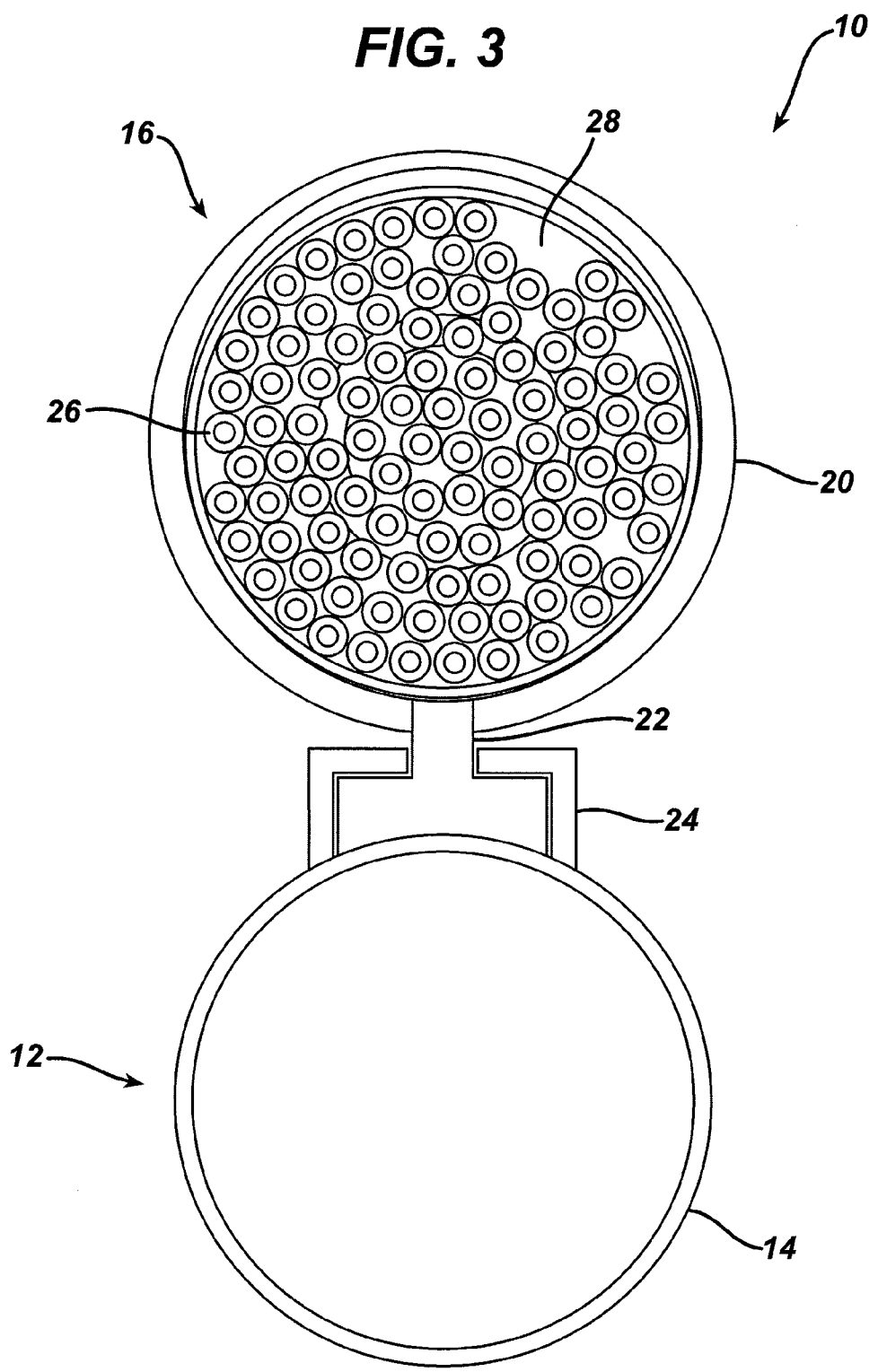
FIG. 3 is a semi-transparent front view of the apparatus of FIG. 1.
Figure 4:
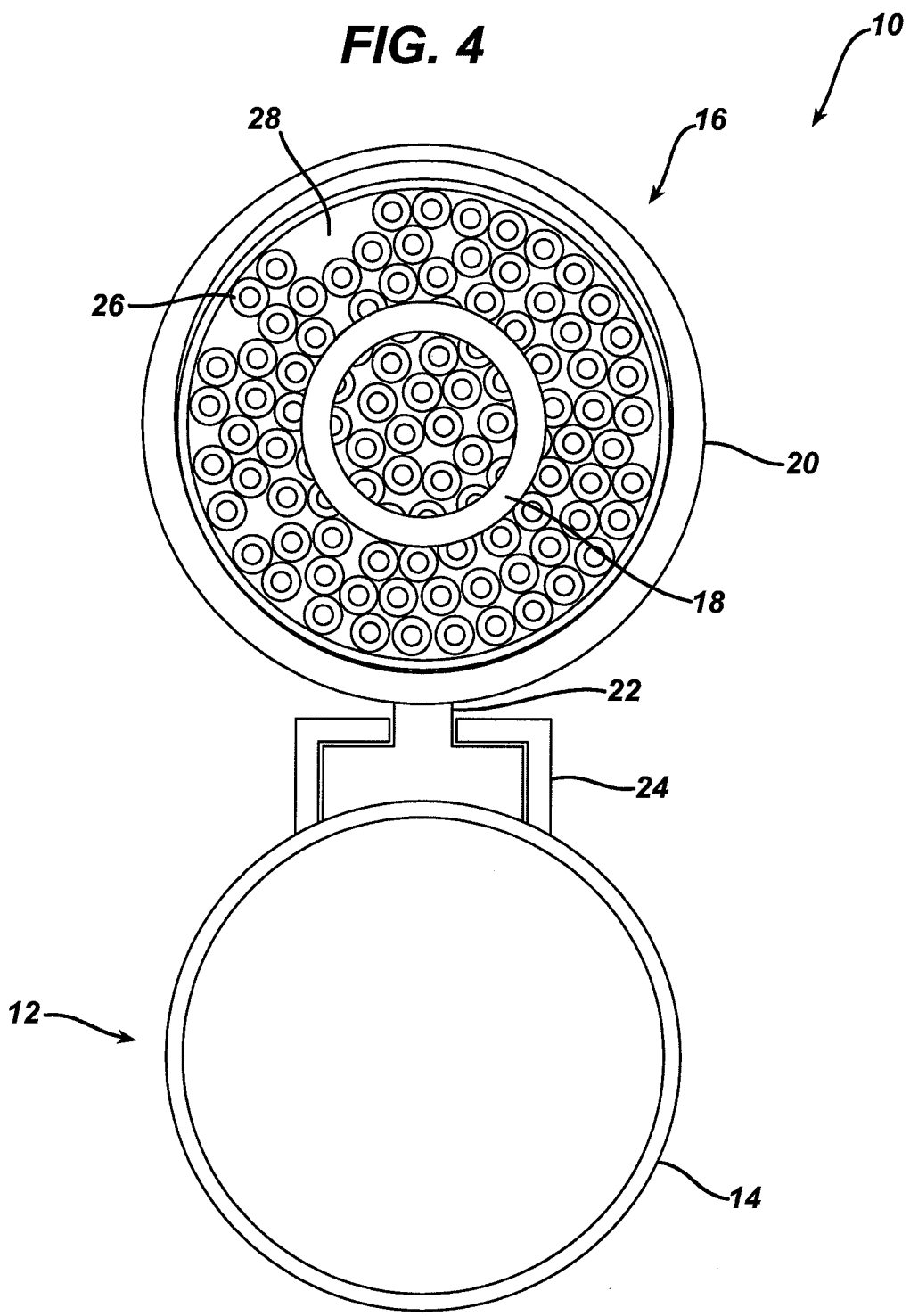
FIG. 4 is a semi-transparent back view of the apparatus of FIG. 1.

As illustrated in FIGS. 1, 3, and 4, the sheath 20 can include one or more elements disposed therein and configured to be engaged and constrained by the sheath 20 when a vacuum force is applied thereto to selectively stiffen the stiffening element 16. While various elements can be used, in an exemplary embodiment the sheath 20 includes a plurality of elongate members 26 or discrete elements located within at least a portion thereof.

In one embodiment, a plurality of elongate members 26 extend through the entire length of the sheath 20. Any number of elongate members 26 can be used, and the number selected will be dependent on a variety of factors, such as the material used, the shape and size of each member 26, and the flexibility or stiffness of each member. Furthermore, the elongate members 26 can have any size and shape that allows them to be disposed, at least partially, in the sheath 20. In one exemplary embodiment the elongate members 26 are flexible, thin, and non-elastic. The elongate members 26 can be made of a material with a high coefficient of friction, for example, a coefficient of friction in the range of about 0.8 to 2. In a preferred embodiment, the coefficient of friction is about 2. For example, the elongate members 26 can be made of steel. Although the thickness of the elongate members 26 can vary, in an exemplary embodiment the elongate members 26 have a thickness of about 0.5 millimeters. The elongate members 26 also have a length that can vary depending on the desired use. The length of the elongate members 26 can be approximately shorter, longer, or the same size as the length of the sheath 20. In the illustrated embodiments the length of the elongate members 26 is slightly less than the length of the sheath 20. In other embodiments the length of the elongate members 26 can be approximately half as long, or less than half as long, as the length of the sheath 20. In one exemplary embodiment the length of the elongate members 26 can be about 1 meter. Further, the length of each elongate member 26 does not have to be the same. The elongate members 26 can taper at their respective ends, much the same way bristles on a paint brush taper, or they can have a random assortment of lengths.

The elongate members 26 can have a variety of different configurations that allow them to be stiffened. In one exemplary embodiment of a stiffening element 16', illustrated in FIG. 2A, the elongate members 26' are in the form of circular wires 30. In another exemplary embodiment of a stiffening element 16", illustrated in FIG. 2B, the elongate members 26" are in the form of planar strips 32. The planar strips 32 in the sheath 20" can allow for bending in only a single plane. This can be accomplished, for instance, by forming the strips 32 such that a height of the strip 32 is less than a width of the strip 32. Accordingly, bending can occur in a first direction, i.e. along the width, while bending can be prevented in a second direction, i.e. along the height.

The elongate members 26 can also be configured to generate friction therebetween. There are many ways by which the elongate members 26 can generate friction, but by way of non-limiting example, in one embodiment the elongate members can include surface features that increase the friction between adjacent members. For example, surfaces of the elongate members 26 can be made rough, for instance by sand-blasting the surfaces. Other techniques for making a surface rough or cratered can also be used. The surfaces of each of the elongate members 26 can then bind or grip against each other when a vacuum force is applied. The surface features can be such that the elongate members 26 can continue gripping each other even after the outside force is no longer applied, or alternatively, such that the gripping ceases when the outside force is no longer applied.

The elongate members 26 can be arranged within the sheath 20 in a variety of ways. In an exemplary embodiment the elongate members 26 can be located at a distal end of the stiffening element 16. The elongate members 26 can be configured to be anchored to a portion of the sheath 20, including an end of the sheath 20, or alternatively, they can remain free. Further, the elongate members 26 can substantially fill a volume of the sheath 20. However, it is preferable to have some space between the elongate members 26 and/or between the elongate members 26 and the sheath 20 to allow the elongate members 26 to slidably move and flex and to be engaged by the sheath 20 when a vacuum force is applied thereto. In one embodiment the elongate members 26 are arranged in one or more bundles.

In another embodiment, a plurality of discrete elements, such as granules, beads, or balls, are disposed within the sheath 20. Like the elongate members 26, the discrete elements are configured to be engaged and constrained by sheath 20 when an outside force, such as a vacuum force, is applied thereto to selectively stiffen the stiffening element 16. The discrete elements are different than most of the elongate members 26 in that they do not have to be elongate and thus do not need much of a length. Nevertheless, they serve the same purpose as the elongate members 26, i.e. they allow for selectively stiffening of the stiffening element 16.

The discrete elements can be made of a material with a high coefficient of friction, for example, a coefficient of friction in the range of about 0.8 to 2. In a preferred embodiment, the coefficient of friction is about 2. For example, the discrete elements can be made of steel. Although the diameter of the discrete elements can vary, in an exemplary embodiment the discrete elements have a diameter of about 0.5 millimeters. The discrete elements can also be adapted to generate friction, in the same manner as is described above and below with respect to the elongate members 26.

The discrete elements can be arranged within the sheath 20 in a variety of ways. In an exemplary embodiment the discrete elements can be located at a distal end of the stiffening element 16. Similar to the elongate members 26, the discrete elements can be configured to be anchored to a portion of the sheath 20, including an end of the sheath 20, or alternatively, they can remain free. Further, the discrete elements can substantially fill a volume of the sheath 20. However, again similar to the elongate members, it is preferable to have some space between the discrete elements to allow the discrete elements to move and be engaged by the sheath 20 when a vacuum force is applied thereto. While the sheath 20 can hold some or all of the discrete elements, the sheath 20 can also include one or more chambers within the sheath 20. Some or all of the discrete elements can be disposed in the chambers, and further, each chamber can be configured to selectively stiffen as desired by the operator. Any number of discrete elements can be used in the sheath 20 or the one or more chambers, and the number selected will be dependent on a variety of factors, such as the material used, the shape and size of each discrete element, and the flexibility or stiffness of each discrete element. Further, chambers can also be used with the elongate members 26, or other types of elements disposed within the sheath 20.

Although the remaining description will primarily discuss the elongate members 26, a person skilled in the art will recognize that the discrete elements could also be incorporated with or used instead of the elongate members in the described embodiments.

A person skilled in the art will recognize that the plurality of elongate members 26 and/or the discrete elements can be retained within the sheath 20 using a variety of techniques. For example, caps, cones, inserts, or other similar type ends can be placed on or within one or both ends of the sheath 20 to retain the ends of the elongate members 26 in a fixed position and or/to prevent the elongate members 26 from puncturing the sheath 20. In the embodiment shown in FIG. 1, the sheath 20 includes first and second end caps 28. The caps 28 can have any shape and size, but in one embodiment they have a flat end portion. Alternatively, the sheath 20 can terminate at a small, circular point and/or a cover or sleeve can be placed around the elongate members 26 to create a layer between the sheath 20 and the elongate members 26.

The elongate members 26 can be connected to the sheath 20 or to the caps 28 by a variety of mechanisms. By way of non-limiting examples, a wire can be disposed between the cap and the elongate members 26 or between the sheath 20 and the members 26.

One skilled in the art will appreciate that a variety of different forces can be used to maintain the stiffening element 16 in a desired fixed position. In an exemplary embodiment, however, the outside force is a vacuum force, although it is recognized that other forces that are capable of maintaining the stiffening element 16, and in particular components of the stiffening element 16 such as the sheath 20 and/or the elongate members 26, in a desired fixed position. In the illustrated embodiment the vacuum force can be applied to a proximal end 16p of the stiffening element 16 by way of a port 18. The stiffening element 16 can be configured such that the vacuum force can be applied to the entirety of the stiffening element 16 or to designated locations within the stiffening element 16, thus providing for selective stiffening. While a single port may be used to provide selective stiffening, multiple ports can also be used. For example, multiple ports can be located at selected locations within or along the stiffening element 16, each being configured to receive a vacuum force. Then, a vacuum force can be selectively applied to the multiple ports to provide selective, localized stiffening at various desired locations of the stiffening element 16.

Applying the vacuum force can remove air from the stiffening element 16 and can cause the sheath to compress around the elongate members 26 thereby constraining the elongate members 26 to hold them in a fixed position relative to one another. When the sheath 20 and the elongate members 26 are in the respective stationary positions, the stiffening element 16 is considered to be stiffened, and accordingly, the stiffening element 16 can hold a desired shape. As previously indicated, the elongate members 26 can include surface features that can help prevent sliding movement between the elongate members when in the stiffened position. Relieving the vacuum force can cause the elongate members 26 and the sheath 20 to no longer be constrained thus allowing free movement of the elongate members 26 and the sheath 20. When either or both of the sheath 20 and the elongate members 26 are not constrained and no longer in the respective stationary locations, the stiffening element 16 is considered to be unstiffened. Alternatively, in some configurations the elongate members 26 and/or the sheath 20 can remain stiffened even after the vacuum force is relieved. For example, the elongate members 26 can be configured to hold a particular position even after the outside force is no longer applied, or alternatively, the stiffening element 16 can be sealed such that the vacuum force can no longer be applied but the stiffening element 16 maintains its position. In such configurations, the elongate members 26 and/or the sheath 20 can be configured to remain in the respective stationary positions in a number of different manners. By way of non-limiting example, the sheath 20 can be made of a deformable material that holds its shape once it has been compressed. By further way of non-limiting example, the elongate members 26 can be configured to lock against each other when compressed together such that they remain locked together even after the force that caused the compression is removed.

Although the stiffening element 16 can be used with most any sort of device, and in particular devices that are used in minimally invasive procedures, in the embodiment shown in FIG. 1, the stiffening element 16 is used with an insertion element 12. The insertion element 12 can be a flexible elongate shaft, and it can include a variety of components. In the illustrated embodiment the insertion element 12 is an endoscope 14 having a working channel 24 for receiving various surgical instruments. In another embodiment the insertion element 12 can be a sleeve configured to be disposed around, or configured to receive, any number of surgical instruments, including, for example, an endoscope. The insertion element 12 can have any length, and the length will likely depend, at least in part, on the desired use, as well as the length and construction of the stiffening element 16. A person skilled in the art will appreciate that the stiffening element can be used to stiffen any device that is inserted into the body.

The stiffening element 16 and the insertion element 12 can be mated together using a variety of different techniques. In an exemplary embodiment, the stiffening element 16 is slidably coupled to at least a portion of the insertion element 12. Either or both of the stiffening element 16 and the insertion element 12 can include a mating element configured to slidably mate the two components. In the illustrated embodiment, the stiffening element 16 includes a T-shaped rail 22 formed along an external length thereof and slidably mated to a complimentary track 24 extending along an external surface of the insertion element 12. A person skilled in the art will appreciate that the insertion element 12 can include the rail 22 and the stiffening element 16 can include the track 24 to receive the rail 22. The association between the insertion element 12 and the stiffening element 16 can be such that when the stiffening element 16 is selectively stiffened and unstiffened, so too is the insertion element 12 based on the location of the insertion element 12 with respect to the location of the stiffening element 16. The location of the insertion element 12 and the stiffening element 16 can be changed by sliding one with respect to the other, or alternatively, by sliding both the insertion element 12 and the stiffening element 16 with respect to each other. Although in the illustrated embodiment the rail 22 and the track 24 are used to slidably couple the stiffening element 16 and the insertion element 12, any number of other mechanical components can be used to mate these two elements 12, 16.

Figure 5A:
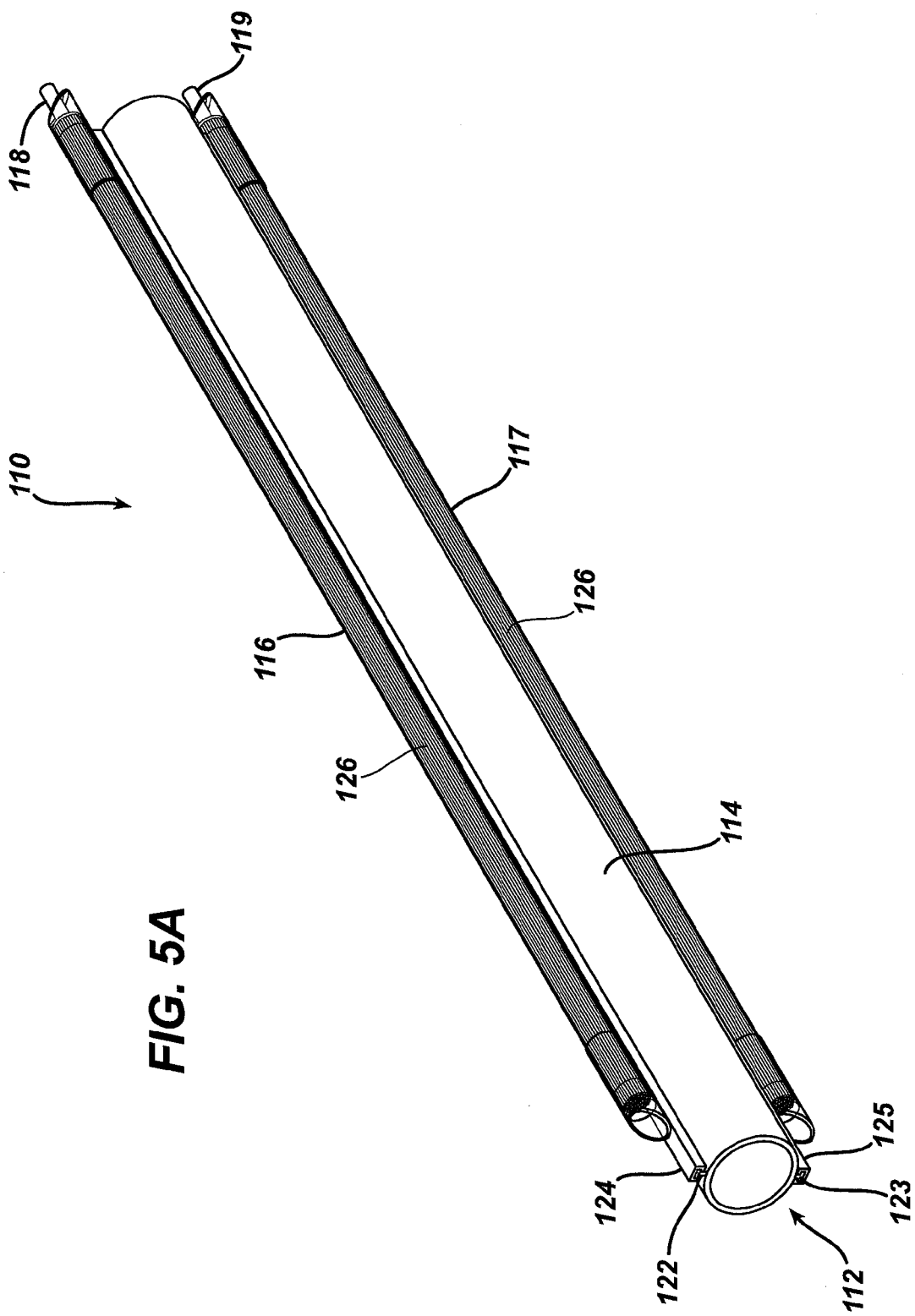
FIG. 5A is a semi-transparent side perspective view of another exemplary embodiment of a surgical device configured for selective stiffening and having two stiffening elements coupled thereto.
Figure 5B:
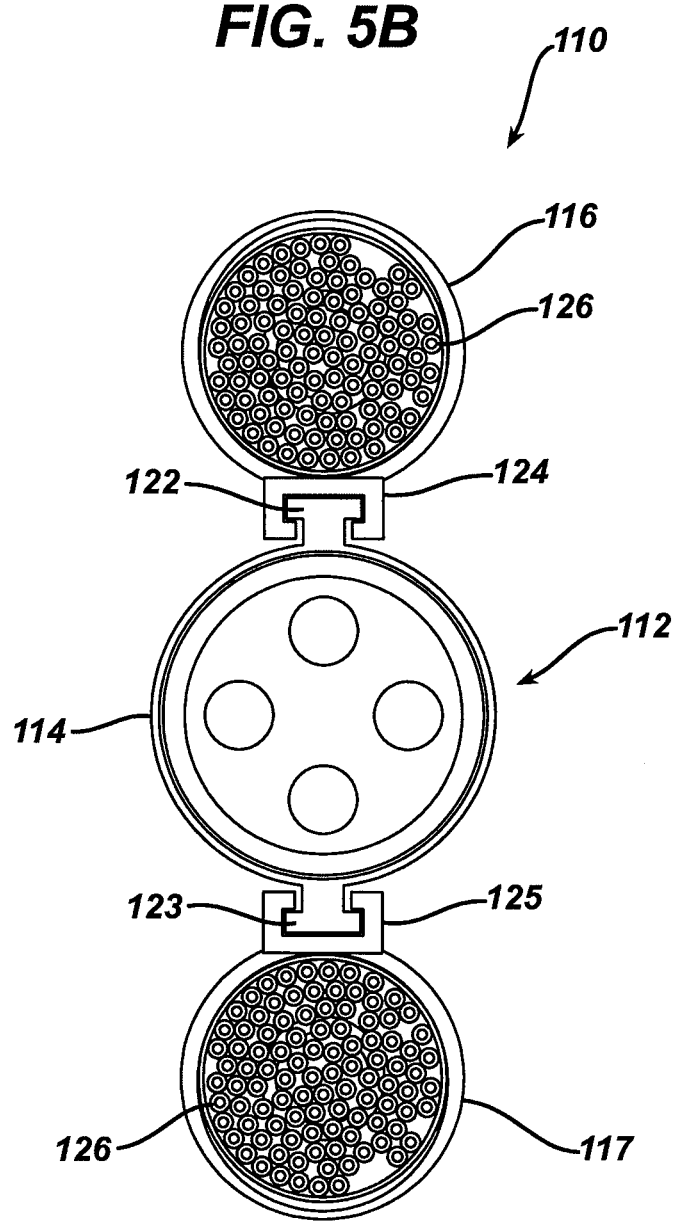
FIG. 5B is a front cross-sectional view of the apparatus of FIG. 5A.

In another embodiment, as shown in FIGS. 5A and 5B, two stiffening elements can be used with a single insertion device. As shown, an insertion element 112 can include rails 122, 123 formed thereon and slidably mated to corresponding tracks 124, 125 formed on stiffening elements 116, 117. Thus, this embodiment, when compared to the embodiments illustrated in FIGS. 1-4, illustrates rails and tracks being interchangeably associated with stiffening elements and insertion elements. The stiffening elements 116, 117 generally have the same properties and features as discussed above with respect to the stiffening element 16, including, by way of non-limiting example, elongate members 126 at least partially disposed therein. Further, each stiffening element 116, 117 can be selectively stiffened, either by the same outside force or by separate outside forces. As illustrated, the separate outside forces are vacuum forces applied through ports 118, 119.

Accordingly, portions of either one of the stiffening elements 116, 117 can be stiffened while portions of the other are not stiffened, or portions of both can be stiffened or unstiffened at the same time.

Figure 6A:
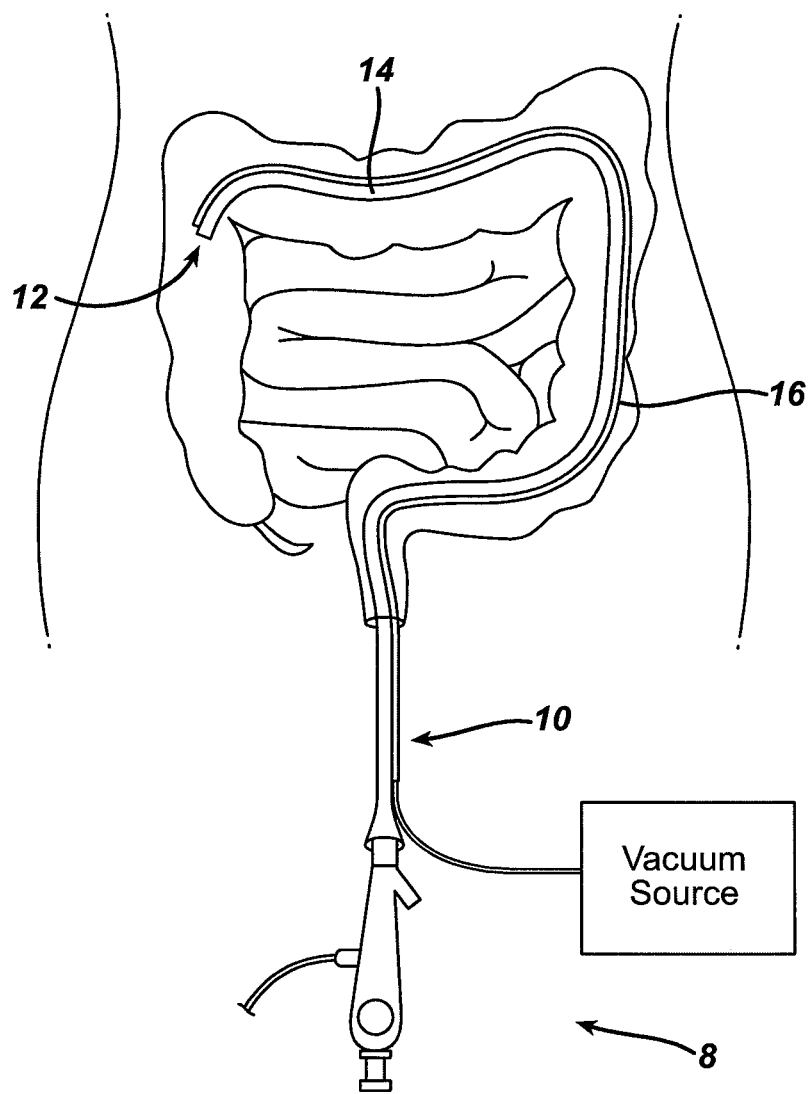
FIG. 6A illustrates one exemplary embodiment of the apparatus of FIG. 1 in use.

Exemplary methods for selectively stiffening a surgical device are also provided. In one embodiment, illustrated by FIGS. 6A-6F and described with respect to a tool 8 that incorporates the device 10 into its design, the insertion element 12 can be inserted into a body 100 and the stiffening element 16 can be slidably coupled to the insertion element 12, by way of rail and track for example, either before, during, or after the insertion element 12 is inserted into the body 100. In an endoscopic surgery, the stiffening element 16 can be coupled to the endoscope 14. The tool 8 includes a vacuum source, which although is illustrated as a separate component can be incorporated to any portion of the tool 8. As illustrated in FIG. 6A, the endoscope 14 and the stiffening element 16 can be placed into the body 100, for example by using a natural body orifice, and directed to any number of desired locations, for instance the peritoneal cavity. In order to arrive at a desired location, portions of the stiffening element 16 can be selectively stiffened as the operator guides the endoscope 14 and the stiffening element 16 through and around organs and other parts of the body 100. The endoscope 14 and the stiffening element 16 can be sequentially moved with respect to each other in order to reach various desired locations, and further, they can be advanced separately or together. The stiffening element 16 can be stiffened before or after either or both of the endoscope 14 and the stiffening element 16 is moved.

Figure 6B:
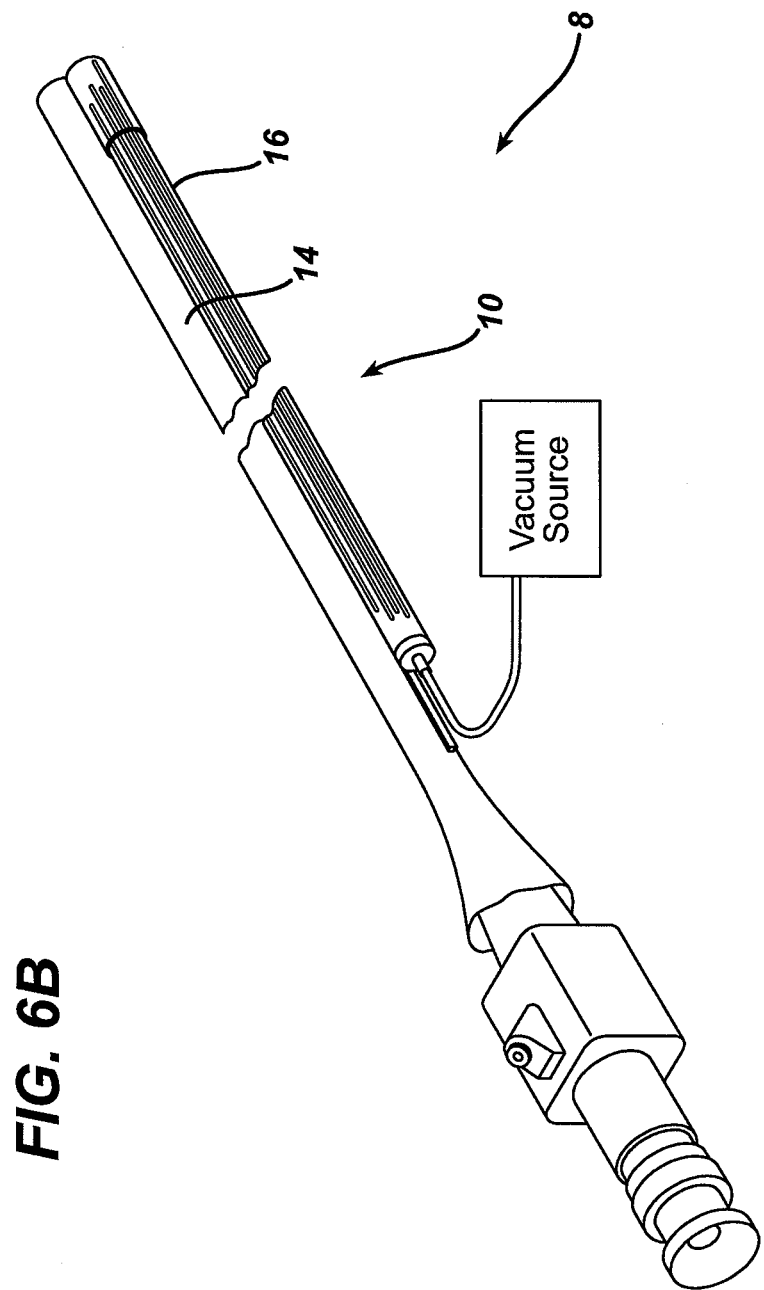
FIGS. 6B-6F sequentially illustrate the exemplary embodiment of FIG. 6A.
Figure 6C:
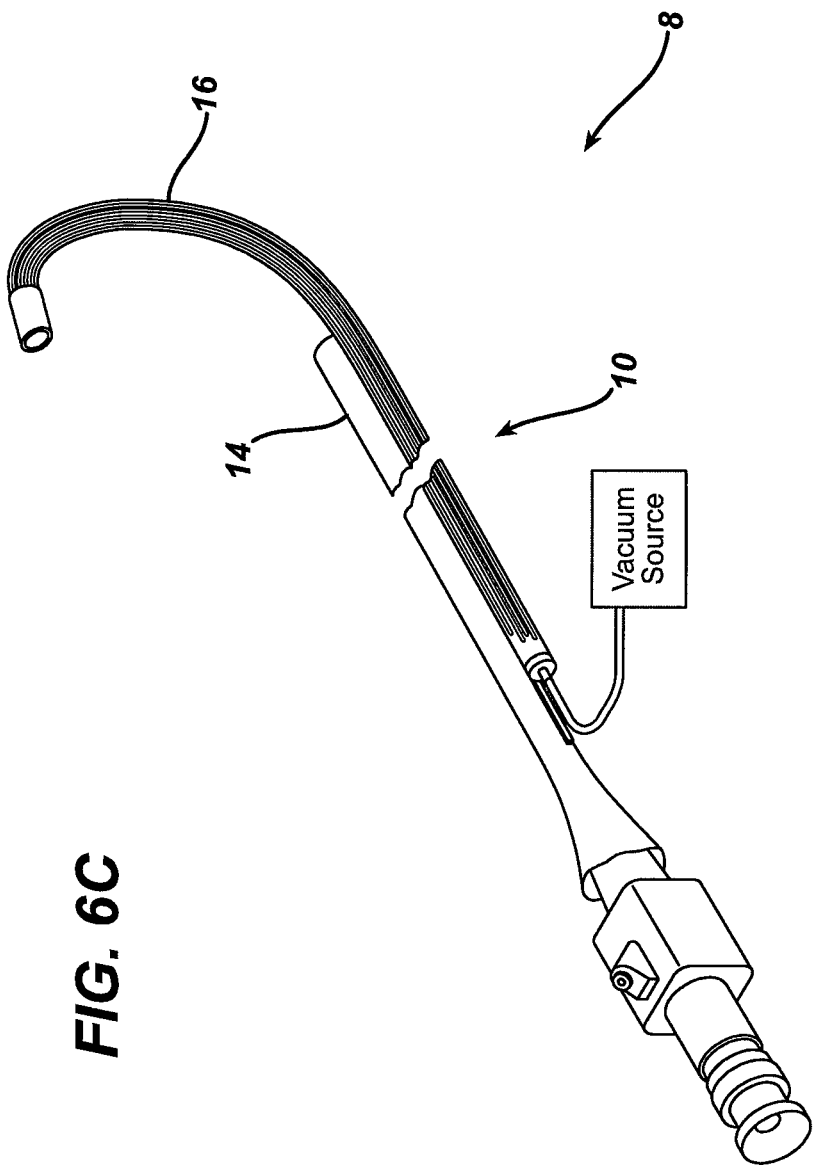
Figure 6D:
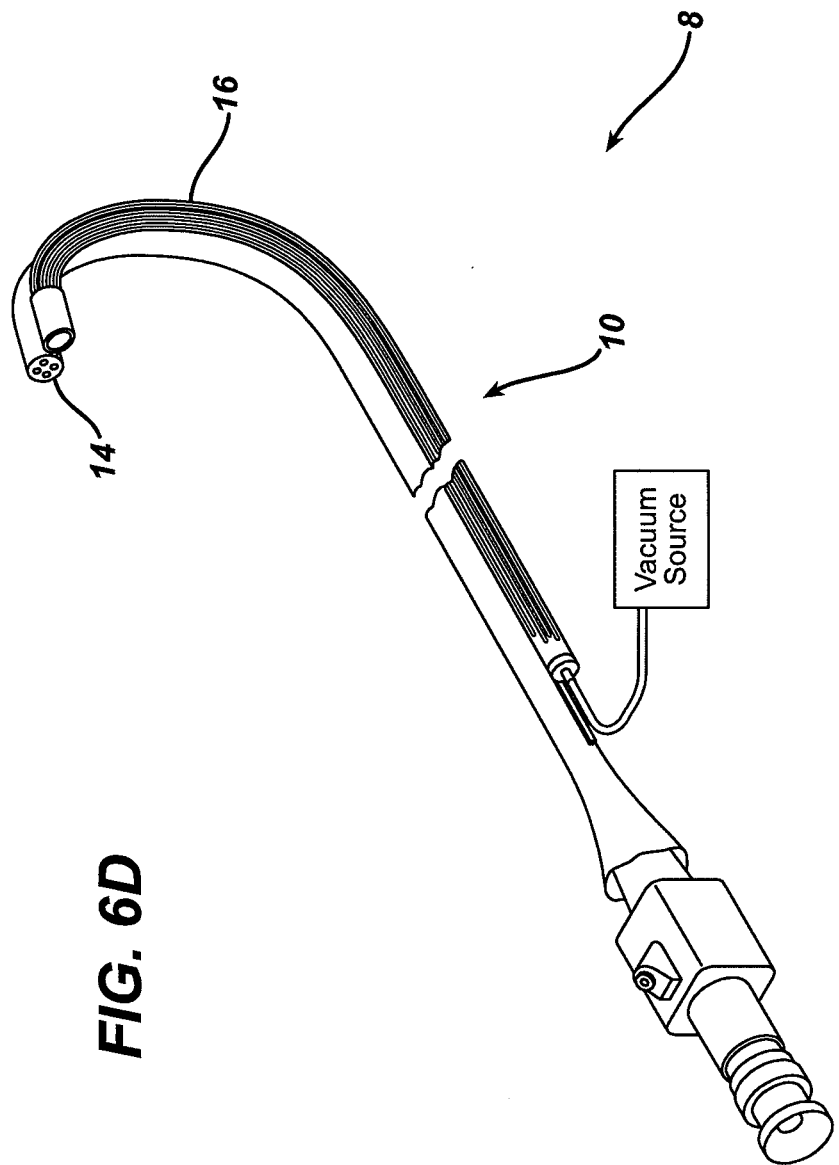
Figure 6E:
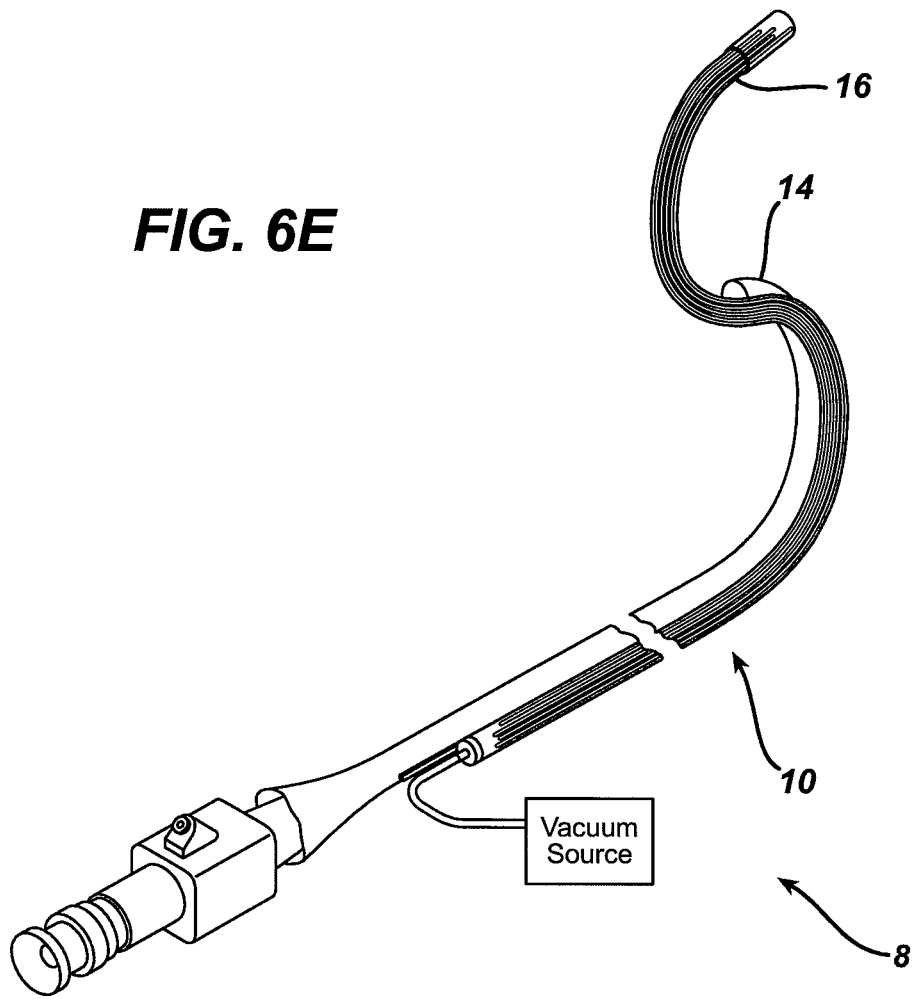
Figure 6F:
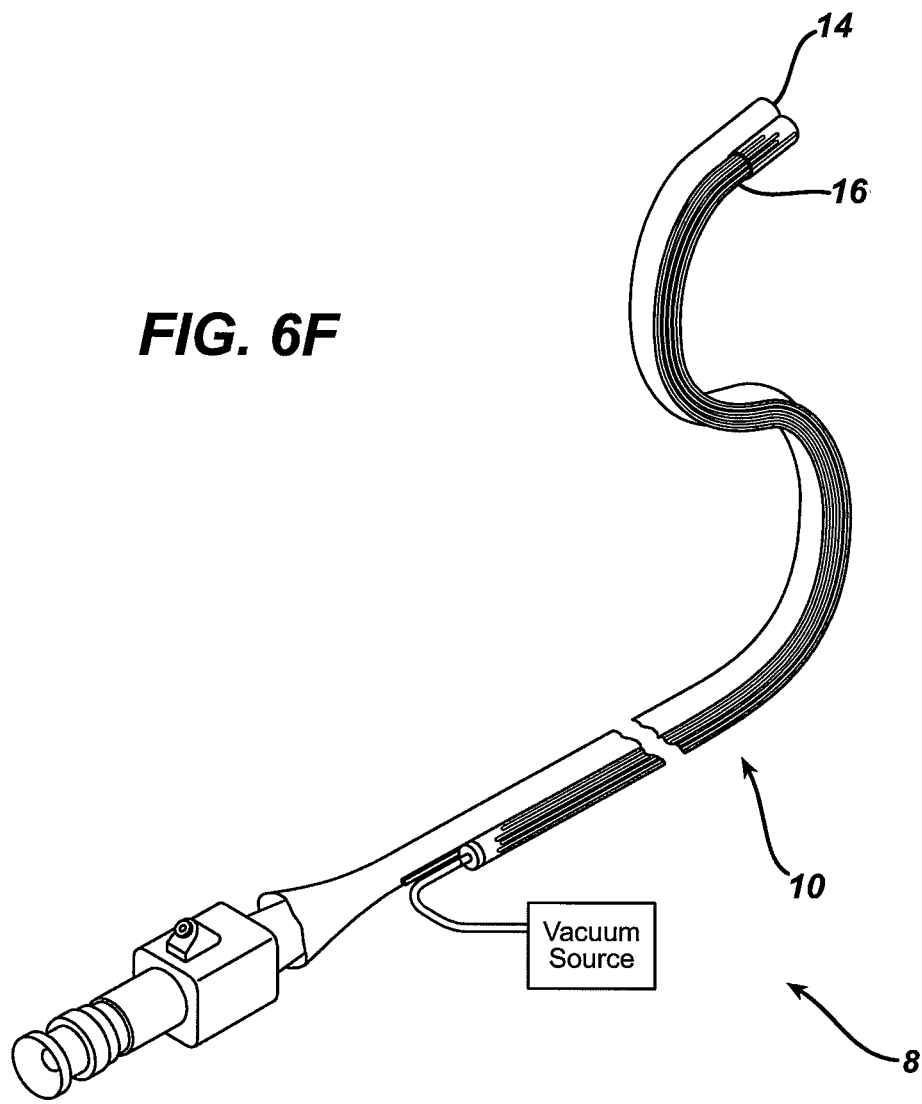

FIG. 6B illustrates the tool before either the endoscope 14 or the stiffening element 16 is flexed. While the endoscope 14 and the stiffening element 16 are shown to be at approximately the same position, they can alternatively be disposed distal or proximal with respect to the other. As illustrated in FIG. 6C, the stiffening element 16 can be moved distally and flexed into a first flexed position while the endoscope 14 remains in its initial position. Alternatively, the endoscope can be advanced distally before, during, or after the movement of the stiffening element 16 to the first flexed position. In FIG. 6D, the endoscope 14 is moved near the first flexed position of the stiffening element 16, although the endoscope 14 can be moved to any desired location proximal, near, or distal to the first flexed position of the stiffening element 16. When the stiffening element 16 is at the first flexed position, an outside force can be applied to the stiffening element 16 to cause at least a portion of the stiffening element 16 to become substantially rigid. When portions of the stiffening element 16 become substantially rigid, the portions of the endoscope 14 that are located near the portions of the substantially rigid stiffening element 16 can similarly be maintained in a desired position. As illustrated in FIGS. 6E and 6F, either or both of the endoscope 14 and the stiffening element 16 can then move, again either separately or together, toward a second position. For example, if the operator desires to use the endoscope 14 at a distance just beyond the first flexed position, the stiffening element 16 can be unstiffened, a distal end of the endoscope 14 can be advanced further to the second position, and then once the second location is reached, the stiffening element 16 can again be stiffened to maintain the second position of the endoscope 14. In such an instance, the stiffening element 16 can also be moved to a new position, but it does not have to be so moved, depending on the desired use. The alternate movement of the endoscope 14 and the stiffening element 16 can be repeated in a variety of orders to advance, navigate, or retrieve the endoscope 14 in and/or from the body 100.

As illustrated in FIGS. 7A-7F, a tool 108 that incorporates the device 110 into its design can also be operated in a body 100 in a similar manner as tool 8 that incorporates device 10, however, because device 110 includes two stiffening elements 116, 117, the device 110 has additional capabilities. The use of two stiffening elements 116, 117 can allow for an alternative method for moving an insertion element 112, in the illustrated embodiment an endoscope 114, to a desired position. Each of the stiffening elements 116, 117 can be selectively stiffened, either jointly or individually, to assist with moving the endoscope 114 to a desired location. Further, a person skilled in the art will recognize that the teachings with respect to using just one stiffening element, as in tool 8, are equally applicable to the tool 108. Additionally, although the illustrated embodiment depicts a separate vacuum source for the tool 8, the vacuum source can also be incorporated to any portion of the tool 8.

Figure 7A:
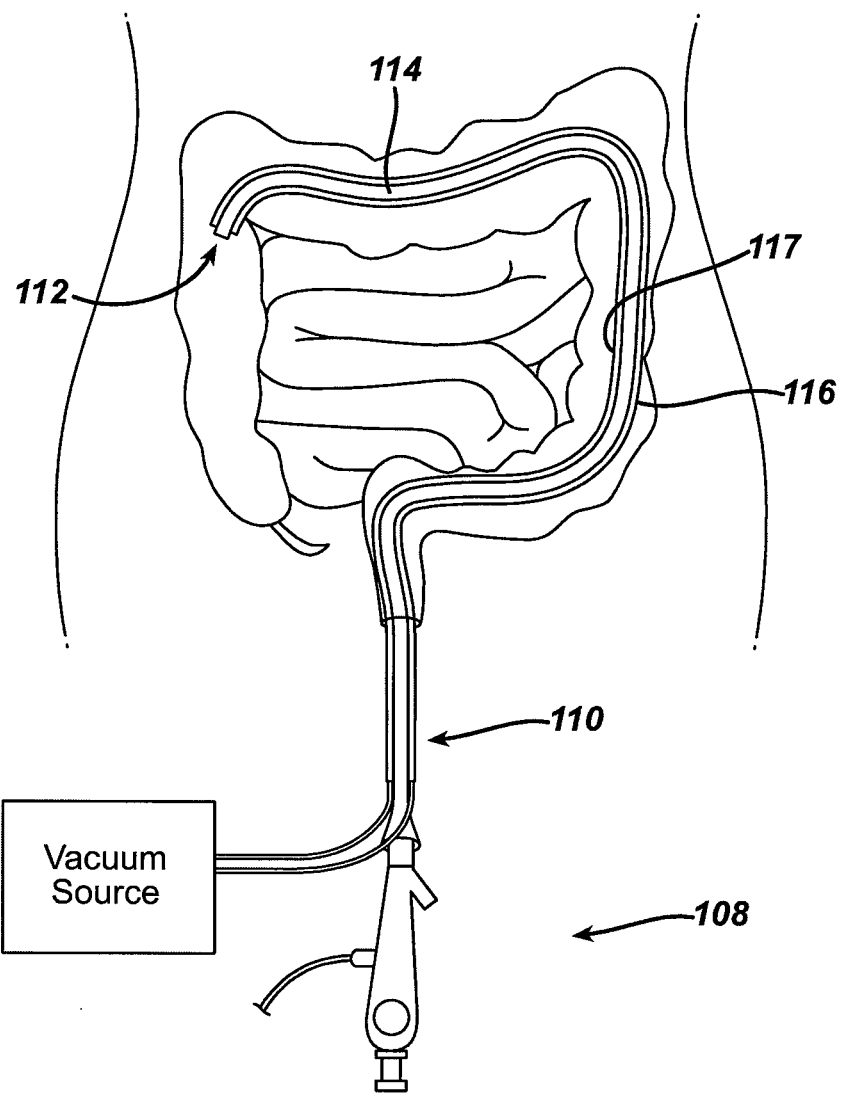
FIG. 7A illustrates one exemplary embodiment of the apparatus of FIG. 5A in use.
Figure 7B:
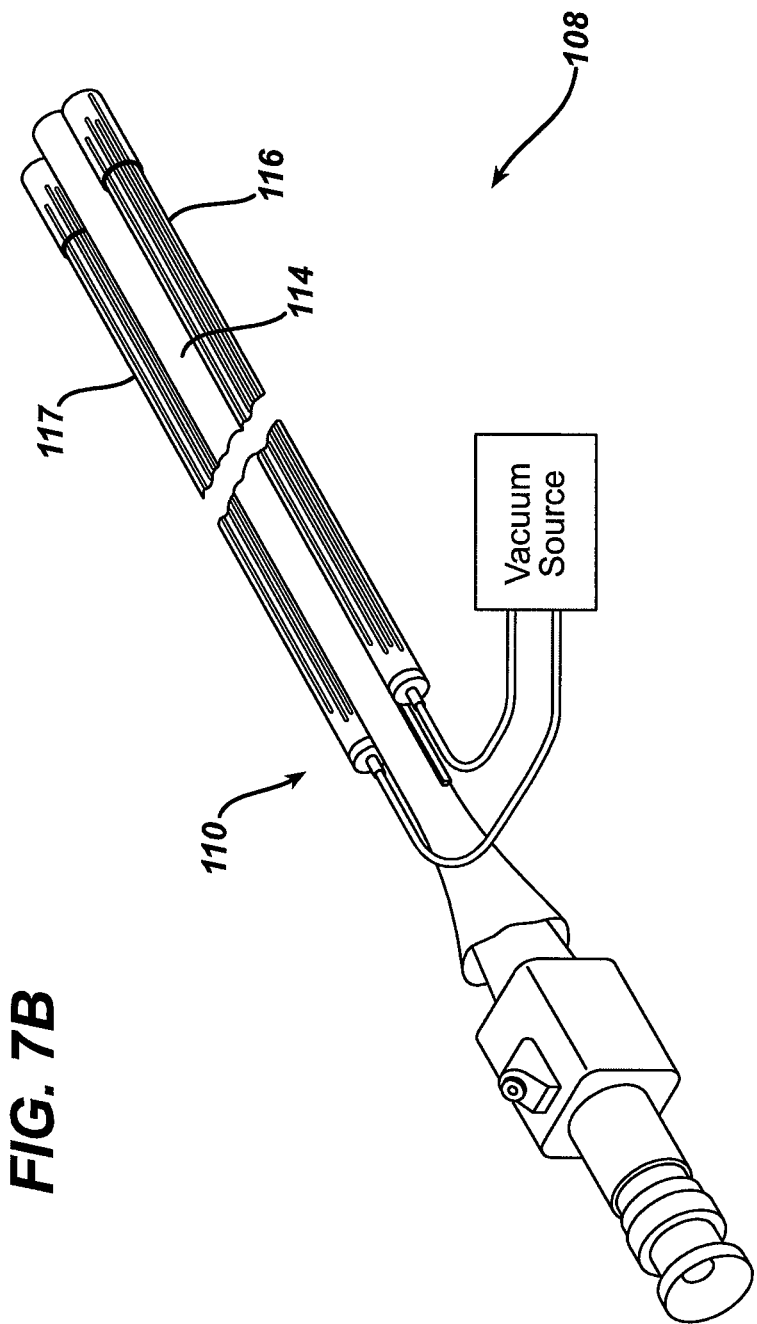
FIGS. 7B-7F sequentially illustrate the exemplary embodiment of FIG. 7A.
Figure 7C:
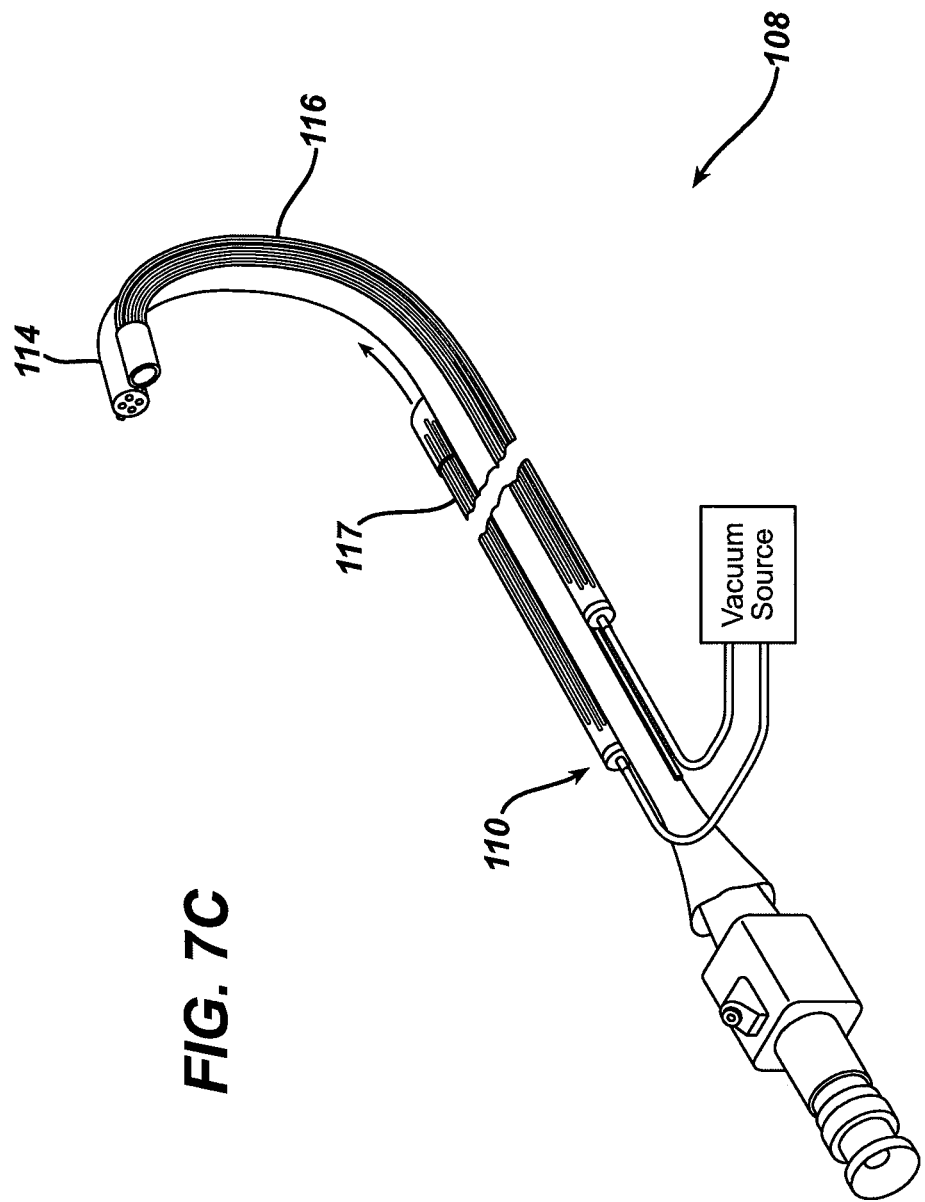
Figure 7D:
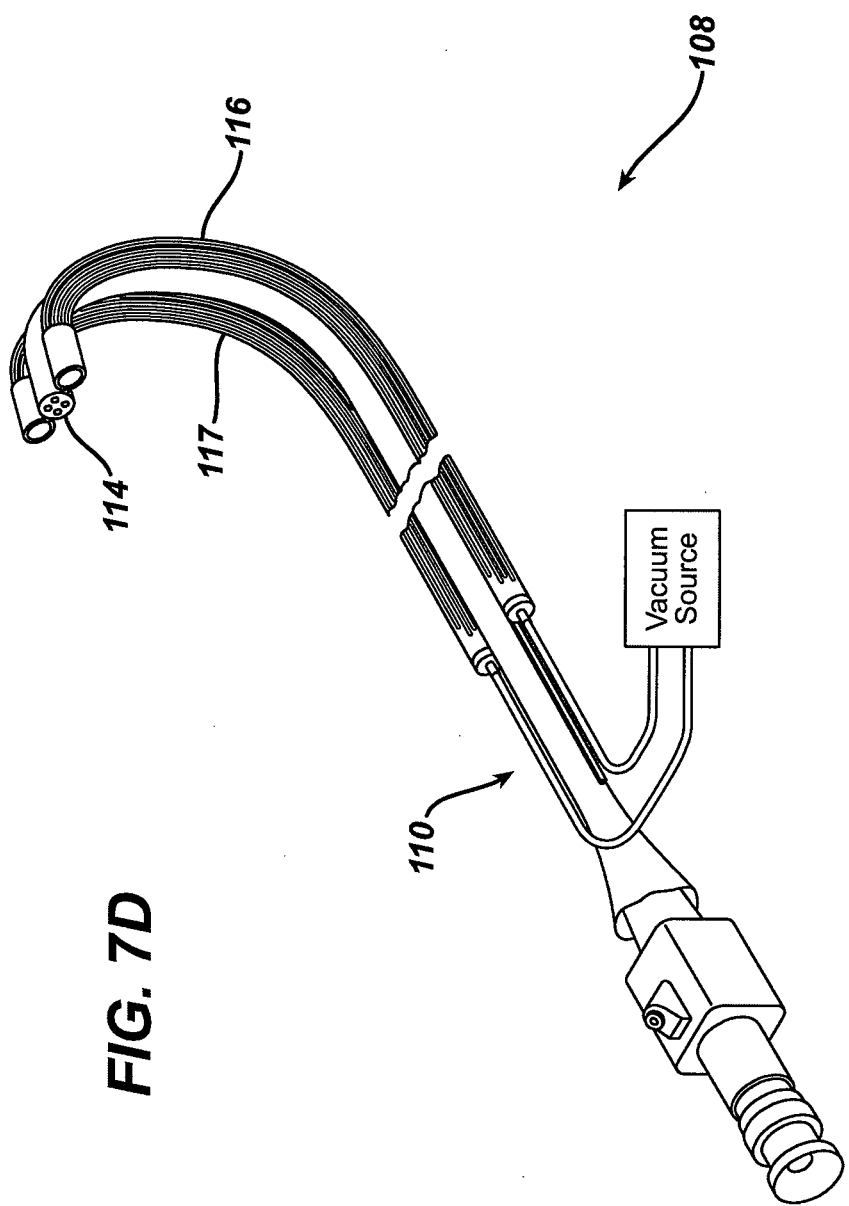

FIG. 7A illustrates the endoscope 114 and the stiffening elements 116, 117 operating in the body 100 at a desired location in a similar fashion as FIG. 6A illustrates with respect to the endoscope 14 and the stiffening element 16. Namely, in the illustrated embodiment the endoscope 114 and both of the stiffening elements 116, 117 can be sequentially moved with respect to each other in order to reach various desired locations, and further, each can be advanced separately or together in any combination. Likewise, any portion of the stiffening elements 116, 117 can be stiffened together or separately, either before or after any of the endoscope 114 or the stiffening elements 116, 117 is moved. FIG. 7B illustrates the tool 108 before any of the endoscope 114 and the stiffening elements 116, 117 are flexed. Subsequently, the first stiffening element 116 can be distally advanced, flexed, and then stiffened to hold the endoscope 114 in a first flexed position, as illustrated in FIG. 7C, and then either before, during, or after the first stiffening element 116 is stiffened, the second stiffening element 117 can be moved distally to approximately the same location as the first stiffening element 116, as illustrated in FIG. 7D, and can be selectively stiffened. Alternatively, in another embodiment, the second stiffening element 117 can be moved to a second flexed position that is more distal than the first flexed position and be selectively stiffened.

Figure 7E:
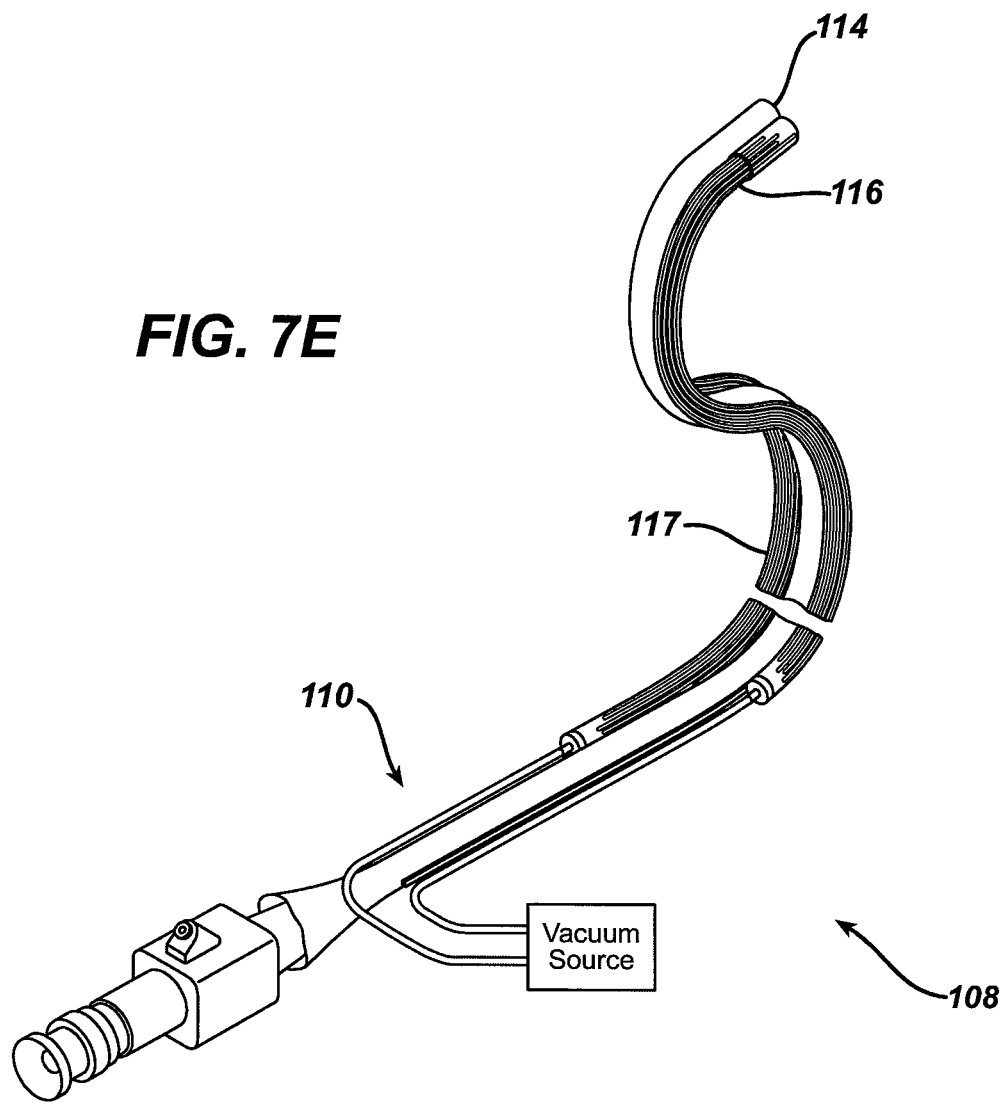
Figure 7F:
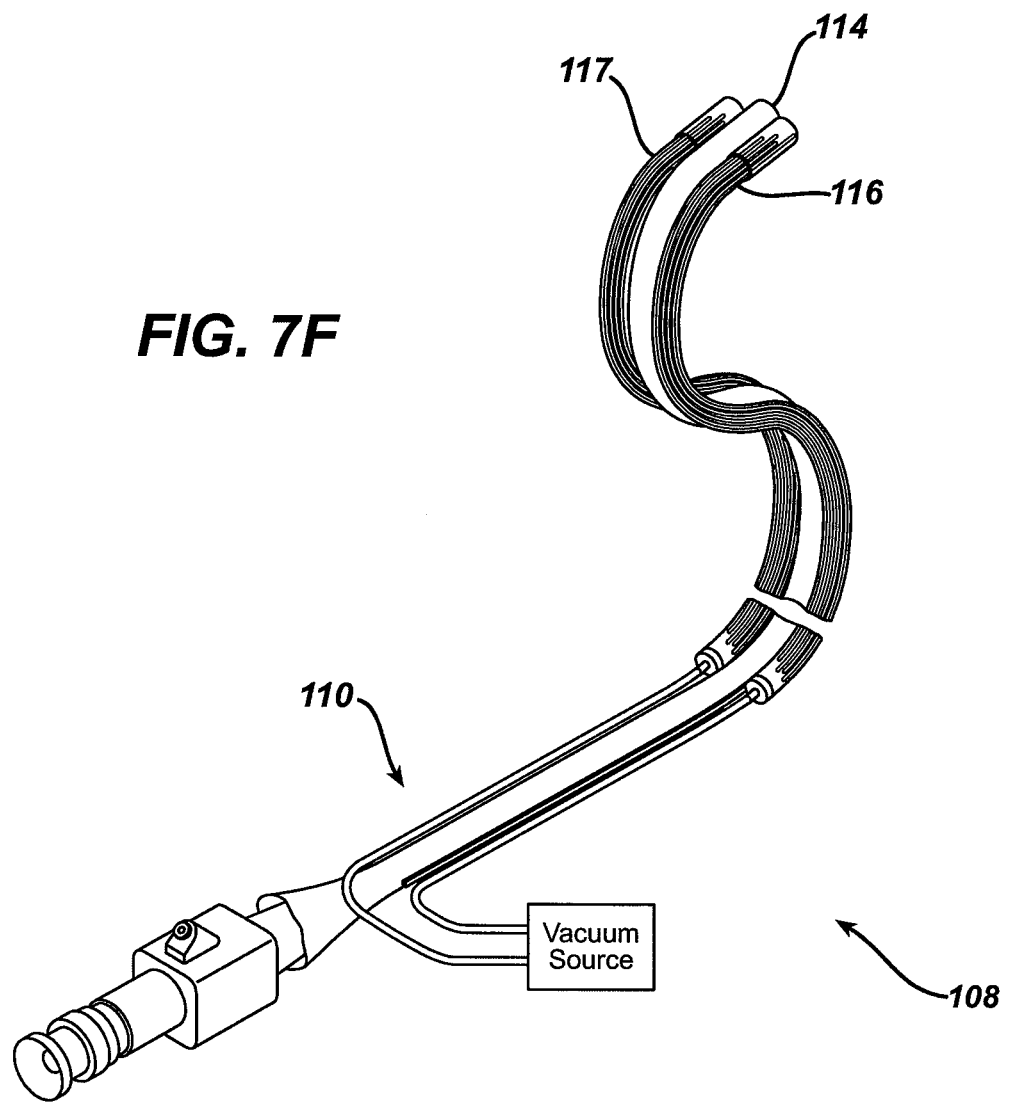

Referring back to the illustrated embodiment, and in particular FIG. 7E, the first stiffening element 116 can be unstiffened, advanced distally, flexed into a second flexed position, and selectively stiffened. When the first stiffening element 116 moves toward or is in the second flexed position, the endoscope 114 and the second stiffening element 117 can be operable to move and/or stiffen in a similar capacity as when the stiffening element 116 was in the first flexed position. For example, the endoscope 114 can be advanced to the second flexed position and the second stiffening element can remain stationary, advance to the second flexed position and be selectively stiffened to provide additional support (as illustrated in FIG. 7F), or it can be advanced to a third location, distal to the second flexed position. Alternatively, the endoscope 114 can be advanced to a third location, distal to the second flexed position.

In fact, although the order of advancement of the endoscope 114 and the stiffening elements 116, 117 is taught in a few different ways, a person skilled in the art will recognize that these orders are merely examples and that many other combinations of advancement can be used. In some instances it may be desirable to always use the same stiffening element to advance to the next position, while in other instances it may be desirable to alternate in some fashion which stiffening element advances to the next position. Selectively moving and stiffening the endoscope 114 and the stiffening elements 116, 117 allows the device 110 to operate in a "leapfrog" like manner, which is discussed in more particularity in U.S. patent application Ser. No. 11/707,831 of Stokes et al., filed on Feb. 16, 2007, and entitled "Flexible Endoscope Shapelock," which is hereby incorporated by reference in its entirety.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device configured for selective stiffening, comprising:
    a flexible elongate insertion element having one of a rail and a complimentary track disposed along at least half of a length thereof;
    a stiffening element extending along at least a portion of the flexible elongate insertion element and configured to selectively stiffen when a vacuum force is applied thereto, the stiffening element including the other of the rail and the complimentary track disposed along at least half of a length thereof such that the rail and the track are coupled to permit sliding movement therebetween, a flexible sheath that forms a length of the stiffening element, and a plurality of elongate cylindrical members independently disposed in and separate from the sheath, each elongate cylindrical member of the plurality of elongate cylindrical members extending along a majority of the length of the stiffening element, and the flexible sheath being configured to radially compress around and engage an outer circumference of the plurality of elongate cylindrical members to prevent movement of the elongate cylindrical members when a vacuum force is applied to the stiffening element, and
    wherein one elongate cylindrical member of the plurality of elongate cylindrical members is capable of contacting another elongate cylindrical member of the plurality of elongate cylindrical members.

2. The surgical device of claim 1, wherein the plurality of elongate cylindrical members are configured to generate friction therebetween.

3. The surgical device of claim 1, wherein the plurality of elongate cylindrical members include a plurality of wires.

4. The surgical device of claim 1, wherein the flexible elongate insertion element comprises an endoscope.

5. The surgical device of claim 1, wherein the flexible elongate insertion element comprises a sleeve configured to be disposed around an endoscope.

6. The surgical device of claim 1, further comprising at least one additional stiffening element extending along at least a portion of the flexible elongate insertion element and configured to selectively stiffen when a vacuum force is applied thereto.

7. A surgical device configured for selective stiffening, comprising:
    an elongate flexible shaft having one of a rail and a complimentary track disposed along at least half of a length thereof; and
    a stiffening element having the other of the rail and the complimentary track disposed along at least half of a length thereof such that the rail and the track are coupled to permit sliding movement therebetween and a plurality of elongate cylindrical members, each elongate cylindrical member of the plurality of elongate cylindrical members being slidably disposed within and extending along a majority of a hollow sheath that forms a length of the stiffening element, the stiffening element being movable between a first position, in which the stiffening element is flexible, and a second position, in which a vacuum force applied to the stiffening element is effective to cause the sheath to radially compress around and engage an outer circumference of the plurality of elongate cylindrical members to rigidly maintain the stiffening element and at least a portion of the elongate flexible shaft coupled thereto in a desired fixed position,
    wherein the stiffening element has closed proximal and distal ends such that the plurality of elongate cylindrical members are retained therein.

8. The surgical device of claim 7, wherein the plurality of elongate cylindrical members are configured to generate friction therebetween.

9. The surgical device of claim 7, wherein the elongate flexible shaft comprises an endoscope.

10. The surgical device of claim 7, wherein the elongate flexible shaft comprises a sleeve configured to be disposed around an endoscope.

11. A method for selectively stiffening a surgical device, comprising:
    inserting a flexible elongate shaft having one of a rail and a complimentary track disposed along at least half of a length thereof into a body cavity;
    selectively sliding the flexible elongate shaft relative to a stiffening element having a sheath that forms a length of the stiffening element and the other of the rail and the complimentary track disposed along at least half of a length thereof, the rail and the track being slidingly mated; and applying a vacuum force to the stiffening element such that at least a portion of the sheath of the stiffening element radially compresses and engages an outer circumference of a plurality of elongate cylindrical members independently disposed in and separate from the sheath of the stiffening element, each elongate cylindrical member extending along a majority of length of the sheath and at least one elongate cylindrical member of the plurality of elongate cylindrical members being capable of contacting another elongate cylindrical member of the plurality of elongate cylindrical members, the application of the vacuum force causing the stiffening element to become substantially rigid and maintain at least a portion of the flexible elongate shaft in a fixed position.

12. The method of claim 11, further comprising moving the stiffening element relative to the flexible elongate shaft.

13. The method of claim 11, further comprising moving the flexible elongate shaft relative to the stiffening element.

14. The method of claim 11, wherein the flexible elongate shaft flexes as it is inserted into the body cavity and the stiffening element maintains the flexible elongate shaft in a flexed position when a vacuum force is applied to the stiffening element.

15. The method of claim 11, wherein the stiffening element comprises a first stiffening element and the method further comprises coupling a second stiffening element to at least a portion of the flexible elongate shaft and applying a vacuum force to the second stiffening element to cause the second stiffening element to become substantially rigid and thereby maintain at least a portion of the flexible elongate shaft in the fixed position.

16. The method of claim 15, further comprising sequentially moving the first and second stiffening element relative to the flexible elongate shaft and sequentially stiffening the first and second stiffening elements with a vacuum force to move the flexible elongate shaft relative to the body cavity.

* * * * *